United States Patent
O'Donnell (10) Patent No.: US 9,770,221 B1
(45) Date of Patent: Sep. 26, 2017

(54) IMAGING USING MULTIPLE ENERGY LEVELS

(71) Applicant: Siemens Medical Solutions USA, Inc., Malvern, PA (US)

(72) Inventor: Thomas O'Donnell, New York, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/200,412

(22) Filed: Jul. 1, 2016

(51) Int. Cl.
  *G06K 9/00* (2006.01)
  *A61B 6/00* (2006.01)
  *A61B 6/03* (2006.01)

(52) U.S. Cl.
  CPC .............. *A61B 6/482* (2013.01); *A61B 6/032* (2013.01); *A61B 6/4014* (2013.01); *A61B 6/4435* (2013.01)

(58) Field of Classification Search
  None
  See application file for complete search history.

(56) References Cited

U.S. PATENT DOCUMENTS

| | | | | |
|---|---|---|---|---|
| 2010/0014628 A1* | 1/2010 | Kadomura | .......... | A61B 6/032 378/4 |
| 2011/0075810 A1* | 3/2011 | Sendai | ................ | A61B 6/4042 378/95 |
| 2011/0280367 A1* | 11/2011 | Baeumer | ................ | A61B 6/032 378/9 |
| 2014/0185896 A1* | 7/2014 | Baturin | .................. | A61B 6/032 382/131 |
| 2016/0120493 A1* | 5/2016 | Maeda | .................. | A61B 6/032 382/131 |
| 2016/0183355 A1* | 6/2016 | Lou | ........................ | A61B 6/482 378/112 |

OTHER PUBLICATIONS

Pavlov, N., Mashlum, G., & Meier, D. (Oct. 2005). Gamma spectroscopy using a silicon photomultiplier and a scintillator. In IEEE Nuclear Science Symposium Conference Record, 2005 (vol. 1, pp. 173-180). IEEE.

Duda, Richard O., Peter E. Hart, and David G. Stork. Pattern classification. John Wiley & Sons, 2001, Chapter 2, Sections 2.5-2.8, pp. 31-51.

Rebuffel, Veronique, and Jean-Marc Dinten. "Dual-energy X-ray imaging: benefits and limits." Insight-non-destructive testing and condition monitoring 49.10 (2007): 589-594.

\* cited by examiner

*Primary Examiner* — Atiba O Fitzpatrick (57) ABSTRACT

A system and method include acquisition of Q (Q≥2) energy images of M (M≥2) different materials, each one of the Q energy images associated with a respective range of photon energies, determination of R (R≥2) combinations of N (N≥2) energy images from the Q energy images, determination of an overlap associated with each of the R combinations of N energy images, the overlap associated with a combination of first N energy images indicating an extent of overlap between distribution functions associated with each of the M different materials and determined based on the first N energy images, and identification of one of the R combinations of N energy images associated with a smallest overlap of the determined overlaps.

20 Claims, 6 Drawing Sheets

IMAGING USING MULTIPLE ENERGY LEVELS

BACKGROUND

In x-ray projection imaging, attenuation is a function of photon energy. The extent of this phenomenon differs among materials. For example, although iodine and calcium exhibit similar x-ray attenuations at high energy levels (e.g., 150 keV), iodine demonstrates a larger increase in x-ray attenuation vis-a-vis calcium at lower energy levels.

Computed Tomography (CT) may exploit this difference via multiple image volumes (i.e., "energy images") acquired based on different ranges of photon energies to facilitate discrimination between the materials. There are several ways to acquire these "energy images." In general, either the spectra emitted from the x-ray tube is changed, as in Dual Energy CT (better described as Dual kV CT), or, as in Photon Counting CT, there is only one incident spectrum but the detector(s) thresholds the photons into different energy categories after they have passed thru the material (i.e., a patient).

The specific method of acquiring the energy images, the energy levels themselves, and the number of different energy images acquired determine the efficiency and/or accuracy of material discrimination. Suitable values differ depending on the available energies, particular materials to be discriminated, and system noise. Systems are desired which provide efficient determination of imaging photon energy level combinations for discriminating two or more given materials.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

Some embodiments provide a computationally tractable means to determine an efficient combination of energy images to discriminate two or more given materials.

The following description is provided to enable any person in the art to make and use the described embodiments and sets forth the best mode contemplated for carrying out the described embodiments. Various modifications, however, will remain readily apparent to those in the art.

Figure 1:
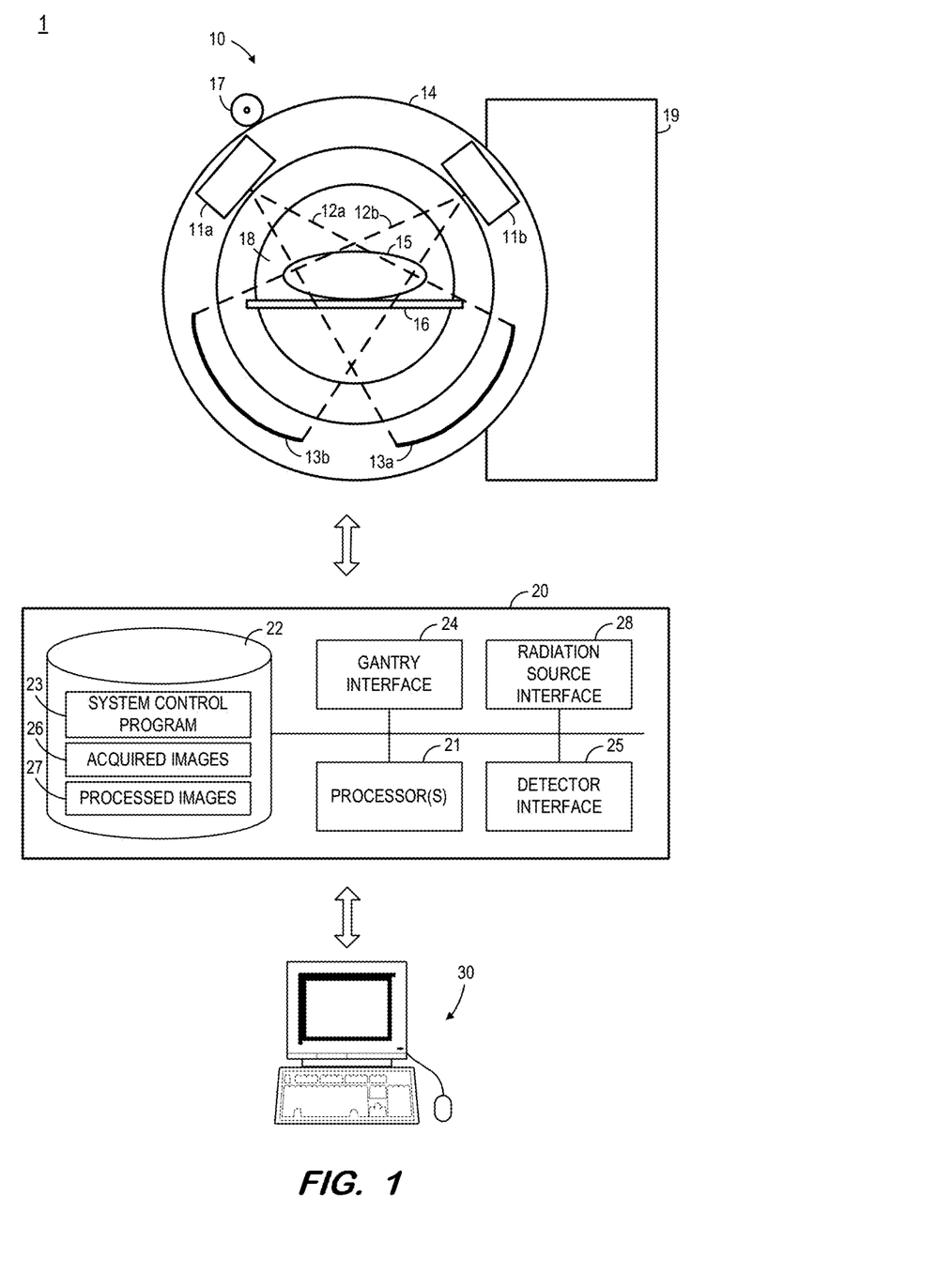
FIG. 1 illustrates an imaging system according to some embodiments.

FIG. 1 illustrates system 1 according to some embodiments. System 1 includes x-ray imaging system 10, control and processing system 20, and operator terminal 30. Generally, and according to some embodiments, x-ray imaging system 10 acquires x-ray images of a patient volume. Control and processing system 20 controls x-ray imaging system 10 and receives the acquired images therefrom. Control and processing system 20 processes the images as described below and provides the processed images to terminal 30 for display thereby. Such processing may be based on user input received by terminal 30 and provided to control and processing system 20 by terminal 30.

Imaging system 10 comprises a CT scanner including X-ray sources 11a and 11b for emitting corresponding X-ray beams 12a and 12b toward opposing radiation detectors 13a and 13b. X-rays source 11a and 11b and radiation detectors 13a and 13b are mounted on gantry 14 such that they may be rotated through 360 degrees while maintaining the same physical relationship therebetween.

In operation, patient 15 is positioned on bed 16 to place a portion of patient 15 between x-ray sources 11a and 11b and their corresponding radiation detectors 13a and 13b. Next, x-ray sources 11a and 11b and their radiation detectors 13a and 13b are rotated by rotation drive 17 around cavity 18 in which patient 15 lies. During this rotation, x-ray sources 11a and 11b are powered by high-voltage generator 19 to transmit x-ray radiation toward detectors 13a and 13b. Detectors 13a and 13b each receive the radiation and produce a set of data (i.e., a raw image) for each projection angle. Embodiments are not limited to CT scanners.

X-ray sources 11a and 11b may comprise any suitable radiation source. In some embodiments, x-ray sources 11a and 11b emit electron, photon or other type of radiation having different ranges of energies. According to some embodiments, x-ray sources 11a and 11b are tubes with rotating anodes exhibiting polychromatic spectra consisting of a continuous spectrum of bremsstrahlung superimposed with characteristic lines of the tungsten material of the anode.

Radiation detectors 13a and 13b may comprise any system to acquire an image based on received x-ray radiation. In some embodiments, radiation detectors 13a and 13b use a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, one or both of radiation detectors 13a and 13b convert received photons to electrical charge without requiring a scintillator layer. The photons are absorbed directly by an array of amorphous selenium photoconductors. The photoconductors convert the photons directly to stored electrical charge.

The charge detected by detectors 13a and 13b represents radiation intensities at each location of radiation fields produced by x-rays emitted from radiation sources 11a and 11b, respectively. The radiation intensity at a particular location of each radiation field represents the attenuative properties of materials lying along a divergent line between detectors 13a and 13b and the particular location of the radiation field. The set of radiation intensities acquired by each radiation detector 13a and 13b therefore represents a two-dimensional projection image of these materials. In some embodiments, several 2D projection images are acquired (i.e., Multidetector CT).

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processors 21 may execute system control program 23 to determine imaging energies based on materials to be imaged, to rotate gantry 14, to cause radiation sources 11a and 11b to emit radiation at desired energies, to control detectors 13a and 13b to acquire images, and to discriminate between imaged materials based on the images. In this regard, system 20 includes gantry interface 24, detector interface 25 and radiation source interface 28 for communication with elements of system 10.

Images acquired from system 10 are stored in data storage device 22 as acquired images 26, in DICOM or another data format. Each acquired image 26 may be further associated with details of its acquisition, including but not limited to imaging plane position and angle, imaging position, radiation source-to-detector distance, patient anatomy imaged, patient position, contrast medium bolus injection profile, x-ray tube voltage, image resolution and radiation dosage.

Processor(s) 21 may execute system control program 23 to process acquired images 26, resulting in processed images 27. Processed images 27 may be provided to terminal 30, and system 20 may also receive input from terminal 30, which may be used to control image acquisition and/or processing of acquired images 26.

Terminal 30 may comprise a display device and an input device coupled to system 20. In some embodiments, terminal 30 is a separate computing device such as, but not limited to, a desktop computer, a laptop computer, a tablet computer, and a smartphone. Terminal 30 displays processed images 27 received from system 20 and receives user input for controlling system 10.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images to terminal 30. Embodiments are not limited to a single system performing each of these functions. For example, system 10 may be controlled by a dedicated control system, with the acquired images being provided to a separate image processing system over a computer network or via a physical storage medium (e.g., a DVD).

Figure 2:
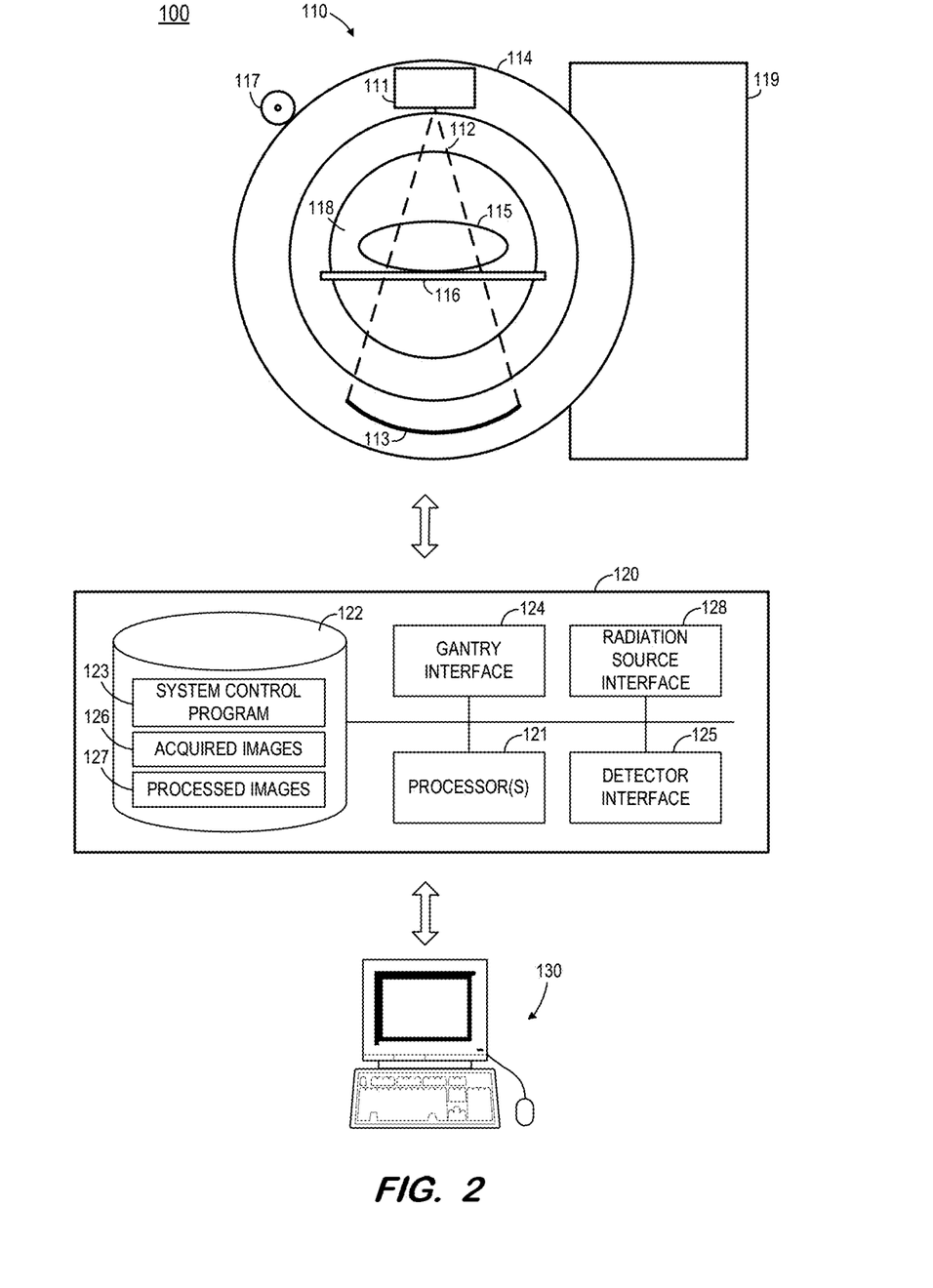
FIG. 2 illustrates an imaging system according to some embodiments.

FIG. 2 illustrates system 100 according to some embodiments. Imaging device 110 includes single x-ray source 111 and detector 113. According to some embodiments, projection images are acquired using different photon energy levels by switching the voltage of x-ray source and reading out the projection data from detector 113 at time points corresponding to each different energy level. In other embodiments, a split filter (e.g., Au and Sn) results in a low-energy half and a high-energy half of the beam incident on the patient (i.e., TwinBeam CT).

However, in some embodiments, detector 113 is capable of acquiring spectral information in order to generate multiple images, each of which corresponds to a different range of photon energies based on a single broad-spectrum radiation emission from source 111. Such a detector 113 may comprise a two-layer or "sandwich" detector with each layer possessing different spectral sensitivities. In some embodiments, however, detector 113 is a photon counting detector.

As described above, conventional detectors measure energy-integrated signals of all received x-ray photons and therefore discard all energy-dependent information. In contrast, photon counting detectors provide energy-specific information relating to received radiation. For example, some known photon counting detectors use pulse-height analysis to record the number of photons of the received energy spectrum that lie within each of specified energy windows.

As described with respect to FIG. 1, patient 115 or another volume is positioned on bed 116 to place a portion of interest of between x-ray source 111 and radiation detector 113. X-ray source 111 is controlled to transmit a spectrum of x-ray radiation toward detector 113 as gantry 114 is rotated around cavity 118. Detector 113 receives the radiation and produces a set of data (i.e., a projection image) for each specified photon energy and at each desired projection angle.

More particularly, an energy image may be created for different energy ranges. The number of different energy images and the specific energy ranges they are created from may be determined as described below. Each energy image describes attenuative properties of intervening materials at the specific photon energy range.

For example, it will be assumed that detector 113 is a photon counting detector. Detector 113 receives the radiation that has passed though the intervening material 115 and produces one energy image representing the photons above 25 keV, one energy image representing the photons above 75 keV, and one energy image representing the photons above 85 keV at each pixel location. As will be described below, these images may be used to discriminate between materials depicted in the images.

Figure 3:
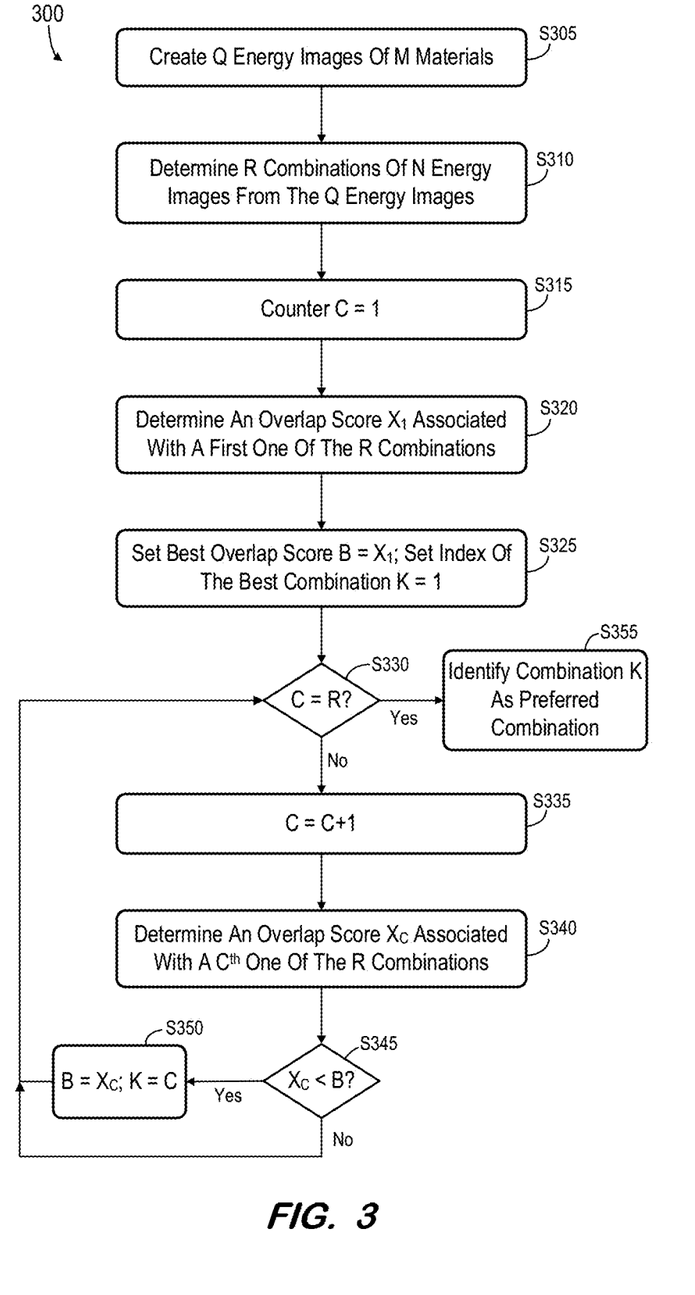
FIG. 3 comprises a flow diagram of a process according to some embodiments.

FIG. 3 comprises a flow diagram of process 300 according to some embodiments. Process 300 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of systems 1 and 100, but embodiments are not limited thereto.

Initially, at S305, Q energy images are created of M ($M \geq 2$) materials. Specifically, each of the Q energy images is acquired based on a range of photon energies. For example, a first energy image may be acquired by detector 13a of imaging system 10 based on photons emitted from source 11a at a first range of photon energies, and a second energy image may be acquired by detector 13b based on photons emitted from source 11b at a second range of photon energies (i.e., Dual kV scanning). In another example, source 111 may emit photons of a spectrum of photon energies, and detector 113 may acquire three (for example) energy images, each corresponding to one of three photon energies using pulse height analysis (i.e., Photon Counting scanning).

Figure 4:
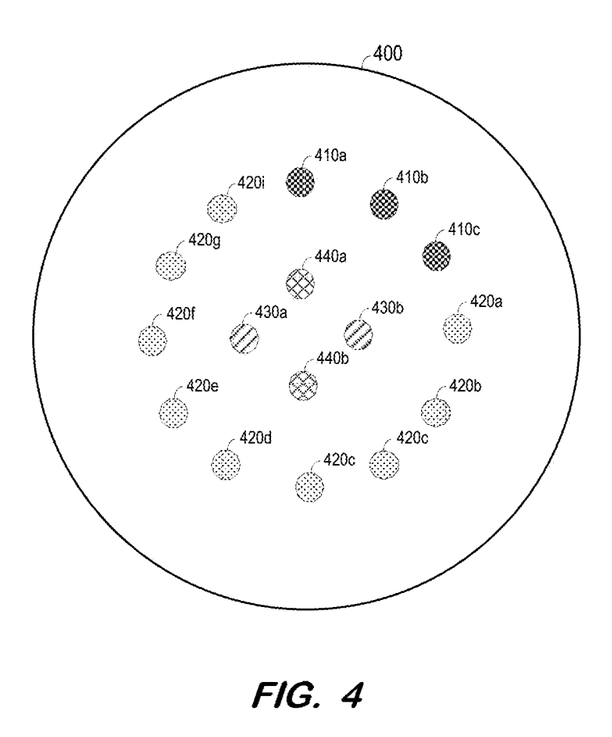
FIG. 4 is a view of disparate materials to be imaged according to some embodiments.

FIG. 4 illustrates materials that may be imaged at S305 according to some embodiments. Sample carrier 400 supports sample containers 410-440. According to the present example, sample containers 410a-410c contain a phosphate buffered saline solution, sample containers 420a-420i contain gold nanoparticles in various concentrations, containers 430a and 430b contain calcium phosphate in solution and containers 440a and 440b contain iodine in solution. Accordingly, in the example of FIG. 4, the number of different materials M=3. Embodiments are not limited to these materials or to the structure and layout of sample carrier 400. In humans, these material regions might correspond to kidney stones. The stones might be uric acid based or oxalate based.

Next, at S310, R combinations of the Q energy images are determined. Using a fixed N representing the number of energies in a combination, the total number of combinations may be represented as Choose(Q,N). Some of these combinations may not be possible or practical. Therefore, a subset of the total number of combinations, having cardinality R is determined at S310. For example, on a photon counting system capable of thresholding at 1-100 keV (Q=100), and with combinations of size N=4, there are 3921225 possible combinations. However the combination (1 keV, 2 keV, 3 keV, 4 keV) is likely not going to be effective for discriminating materials, as the threshold values are so similar, so this combination might be ignored, leaving R=3921224 combinations.

At S315, a counter C is set to 1. The counter C will allow tracking of the combination being evaluated as flow cycles through all R combinations to determine which of the R combinations may be most effective at discriminating the M materials.

At S320, an overlap score is determined for a first one of the R combinations. An example will be described in which N=2 and M=2. Specifically, each of the R combinations will consist of two energy images (e.g., photon counting 50 keV and 90 keV), and two materials (e.g., gold and iodine) are to be discriminated. The first one of the R combinations to evaluate at S320 is assumed to be (50, 90).

Figure 5:
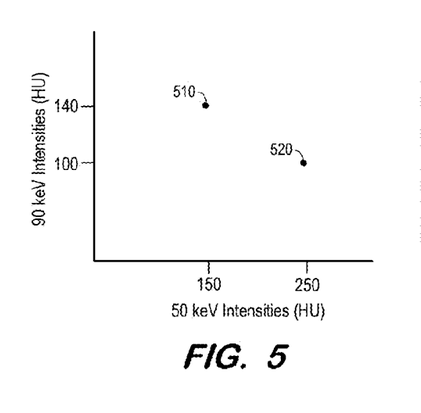
FIG. 5 is a plot of Hounsfield Units (HU) of a given voxel obtained at two different energy levels according to some embodiments.
Figure 6:
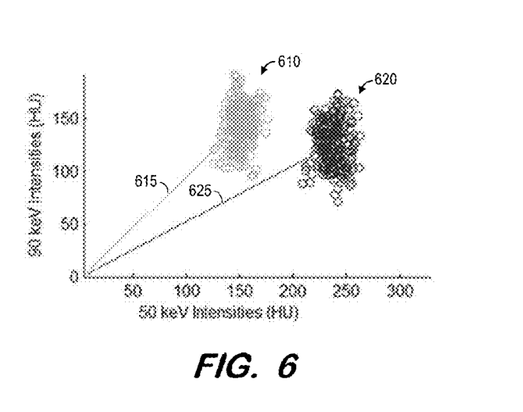
FIG. 6 is a plot of Hounsfield Units of a plurality of voxels of two different materials obtained at two different energy levels according to some embodiments.

FIG. 5 shows a scatter plot of HU values 510 of a single voxel of gold and HU values 520 of a single voxel of iodine. The x-axis of the plot represents a 50 keV energy image and the y-axis represents a 90 keV energy image. As shown, the gold voxel has a value of 150HU in the 50 keV image and 140HU in the 90 keV energy image. The iodine voxel has a value of 250HU in the 50 keV energy image and a value of 100 in the 90 keV energy image. FIG. 6 illustrates the same axes as FIG. 5 and is a scatter plot of the HU values of multiple voxels of each material. The gold voxels 610 and iodine voxels 620 cluster together but are not all the exact same value—this is due to noise in the acquisition process. Lines 615 and 625 are drawn to the centroid of the clusters of each material.

Figure 7:
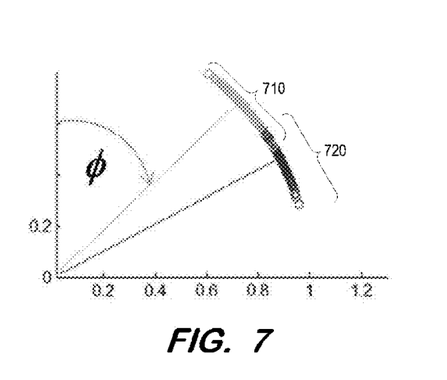
FIG. 7 is a normalized plot of the FIG. 6 distribution according to some embodiments.
Figure 8:
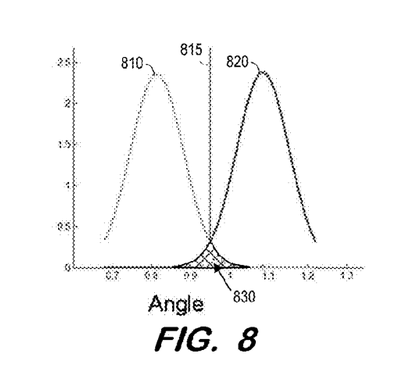
FIG. 8 illustrates distribution functions corresponding to the two materials of FIG. 6 according to some embodiments.

FIG. 7, illustrates the conversion of each of the voxels from FIG. 6 to polar coordinates. The radii for each voxel is normalized to unit length for easier visualization. Voxels 710 correspond to voxels 610 of FIG. 6, and voxels 720 correspond to voxels 620 of FIG. 6. The angles associated with all the voxels of a particular material form a distribution. It is assumed that this is a Normal Distribution and, as shown in FIG. 8, Gaussian distributions 810 and 820 are fit to the angles of each material and plotted. Shaded area 830 represents the overlap between the distributions. The present inventor has advantageously noted that the overlap indicates the ability of the N energy images to discriminate the M materials.

Figure 9:
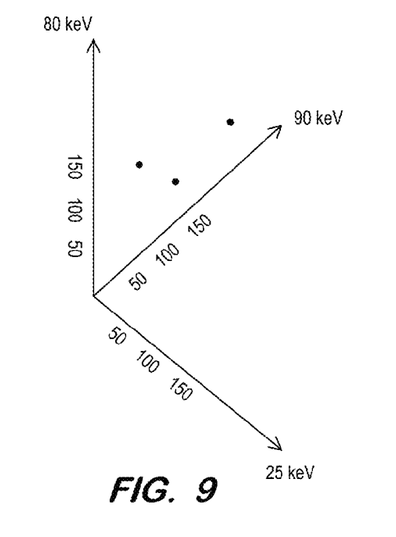
FIG. 9 is a plot of Hounsfield Units of a given voxel obtained at three different energy levels according to some embodiments.
Figure 10:
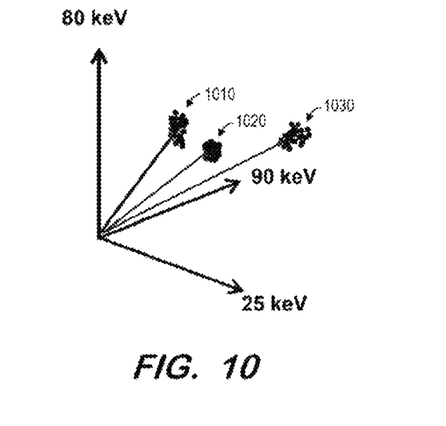
FIG. 10 is a plot of Hounsfield Units of a plurality of voxels of three different materials obtained at a three different energy levels according to some embodiments.
Figure 11:
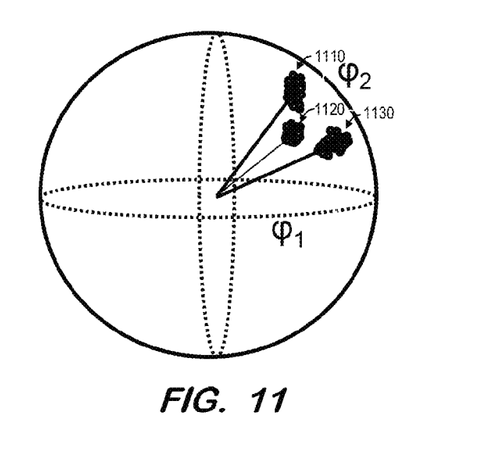
FIG. 11 is a normalized plot of the FIG. 10 distribution according to some embodiments.
Figure 12:
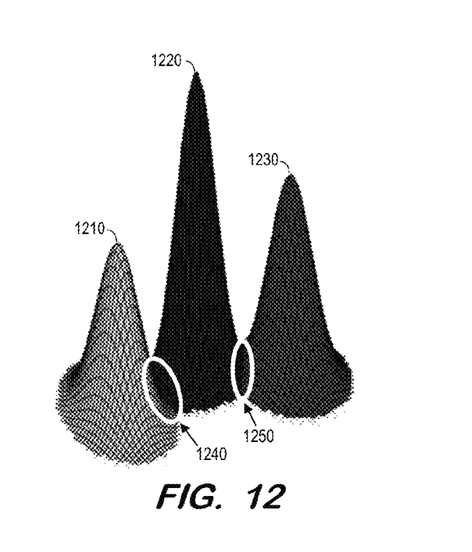
FIG. 12 illustrates distribution functions corresponding to the three materials of FIG. 10 according to some embodiments.

FIGS. 9-12 illustrate a similar process in the case of M=3 materials and N=3 energy images. FIG. 9 shows the HU values of single voxels of three different materials (i.e., gold, iodine, and calcium) plotted in a three-dimensional space described by the three energy images (20, 85, 90) keV. FIG. 10 illustrates the same axes as FIG. 9 but includes multiple voxels 1010, 1020 and 1030 representing each material. In FIG. 11, each of the voxels from FIG. 10 has been converted to spherical coordinates with sweep out angles $\phi_1$ and $\phi_2$. Two-dimensional Gaussian distributions 1210, 1220 and 1230 are fit to the clusters of angles $\phi_1$ and $\phi_2$ and are plotted in FIG. 12. The encircled areas 1240 and 1250 highlight the overlap between the distributions. Again, the extent of this overlap indicates the ability of the particular three energy images to discriminate the three materials.

The aforementioned process may be generalized to any number of materials M≥2 and energy images N≥2. As mentioned above, for N=2 the angular representation of a voxel utilizes polar coordinates. For N=3, the angular representation of a voxel utilizes spherical coordinates. For N≥4, the conversion is to hyperspherical coordinates. The following formula generalizes this conversion to any dimension N≥2.

According to some embodiments, for each material m, each voxel forms a vector in N dimensional space $(x_1, x_2, \ldots, x_n)$. Each voxel is converted into unit hyperspherical coordinates of dimension N−1 as follows:

$$\phi_1 = \arccos\left(\frac{x_1}{\sqrt{x_n^2 + x_{n-1}^2 + \ldots + x_1^2}}\right),$$

$$\ldots \phi_{n-2} = \arccos\left(\frac{x_1}{\sqrt{x_n^2 + x_{n-1}^2 + x_{n-2}^2}}\right)$$

$$\phi_{n-1} = \begin{cases} \arccos\left(\frac{x_1}{\sqrt{x_n^2 + x_{n-1}^2 + x_{n-2}^2}}\right) & \text{if } x_n \geq 0 \\ 2\pi - \arccos\left(\frac{x_1}{\sqrt{x_n^2 + x_{n-1}^2 + x_{n-2}^2}}\right) & \text{if } x_n \geq 0 \end{cases},$$

yielding p voxels per material with coordinates $\phi_1^m \ldots \phi_{n-1}^M$.

For each material cluster, the fitting of the Gaussian distribution may be generalized as follows: the mean $\vec{\mu}$ and covariance matrix $\Sigma$ may then be computed in the $\phi_1^m \ldots \phi_{n-1}^m$ space to create a material-specific distribution function (m dropped for readability):

$$p(\vec{\phi}) = \frac{1}{(2\pi)^{d/2}|\Sigma|^{1/2}} \exp\left(-\frac{1}{2}(\vec{\phi} - \vec{\mu})/\Sigma^{-1}(\vec{\phi} - \vec{\mu})\right)$$

To compute a measure of overlap for M=2 materials, the Bhattacharyya Coefficient (BC) may be used. BC provides an analytic solution for the case of estimating the overlap of two normal distributions corresponding to materials a and b:

$$BC = \exp\left(-\frac{1}{8}(\vec{\mu}_a - \vec{\mu}_b)^t P^{-1}(\vec{\mu}_a - \vec{\mu}_b)\right)\sqrt{\frac{\sqrt{|\Sigma_a||\Sigma_b|}}{|P|}},$$

where $$P = \frac{(\Sigma_a + \Sigma_b)}{2}$$

If M=2, "the overlap score", X, is determined to be equal to BC at S320. If M≥3 BC is computed for each pair of materials. For example, in the case of three materials a, b, and c, BC is computed for (a,b), (b,c), and (a,c). The overlap score X is determined as the maximum BC over all possible pairs.

Returning to FIG. 3, a first overlap score $X_1$ is determined at S320 for a first one of the R combinations of energy images. This score is assigned to B (i.e., signifying the Best score computed thus far) and K (i.e., the index of the combination associated with the Best overlap score) is set to 1.

At S330, it is determined whether C=R. In particular, S330 is a determination of whether an overlap score has been determined for each of the R combinations of energy images. If so, the combination that is associated with the best (lowest) overlap score among all the R combinations is identified at S355 based on the current value of index K.

If C is not equal to R at S330, flow proceeds to S335 to increment the counter C by 1. An overlap score $X_C$ is then determined at S340 for a $C^{th}$ combination of the R combinations.

At S345, it is determined whether the determined overlap score $X_C$ for the current value of C is better (i.e., lower) than B, which, as described above, is the best overlap score determined thus far. If so, B is set to $X_C$ and K is set to C at S350, and flow returns to S330. Flow also returns directly to S330 if it is determined at S345 that $X_C$ is greater than B.

Process 300 therefore cycles through S330 to S350 to compute overlap scores for each of the R combinations of N energy images, writing over best score B and best combination index K each time a best overlap score is determined. Upon termination of process 300 at S355 after it is determined that C=R (i.e., overlap scores have been determined for each of the R combinations), variable holds the best overlap score and variable K holds the index of the combination associated with the best overlap score.

According to some embodiments, the overlap measure might be one of several factors used to determine the set of energy values at S335. For example, some weight may be given to sets including a fewer number of energy levels, to sets including energy levels requiring less operating power, to sets including energy levels which are otherwise more suitable for operation of the imaging device and/or for patient exposure, and/or to any other suitable factor.

The above discussion of process 300 assumes that N, the number of energy images in each combination, is fixed. According to some embodiments, process 300 is executed repeatedly using increasing values of N (e.g., N=2, then N=3, N=4, . . . ). If the Q energy images remain substantially the same, the best overlap score B should decrease (i.e., improve) as N increases. In some embodiments, the value of N may increase until the decrease in the determined best overlap measure between successive iterations of process 300 is less than a threshold amount, indicating that using higher values of N is likely not worth the expense of image acquisition.

According to some embodiments, given an unknown material (i.e., which is believed to be one of M materials), the Gaussian distributions fit to each material (as illustrated, for example, for N=2 in FIG. 8 and for N=3 in FIG. 12) may be used to determine the most probable material identity.

By scanning the unknown material to create N energy images and converting the voxels from those energy images to angular coordinates (i.e., polar coordinates for N=2, spherical coordinates for N=3, etc.), the resultant vector of angles may be evaluated with the Gaussian distributions associated with each material M. The Gaussian distributions serve as probability distributions. The distribution associated with a material with the highest probability implies that the unknown material is the material associated with that distribution. If all the probabilities are low, it may be concluded that the unknown material is not one of the M materials.

By selecting the combination of N energy images providing the lowest overlap score, some embodiments may facilitate efficient material discrimination.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
an interface to:
    acquire Q (Q≥2) energy images of M (M≥2) different materials, each one of the Q energy images associated with a respective range of photon energies; and
a processor to:
    determine R (R≥2) combinations of N (N≥2) energy images from the Q energy images;
    determine an overlap associated with each of the R combinations of N energy images, the overlap associated with a combination of first N energy images indicating an extent of overlap between distribution functions associated with each of the M different materials and determined based on the first N energy images; and
    identify one of the R combinations of N energy images associated with a smallest overlap of the determined overlaps.

2. A system according to claim 1, wherein determination of an overlap associated with a combination of first N energy images comprises:
    determination, for each one of the first N energy images, of values corresponding to voxels representing each of the M materials;
    determination of an N-dimensional coordinate of N values for the voxels of each of the M materials; and
    determination, for each of the M materials, of a distribution function based on the N-dimensional coordinates associated with the M material.

3. A system according to claim 2, the processor further to determine, based on the M distribution functions and on second N energy images of a volume, a material associated with a voxel of the volume,
    wherein the second N energy images are acquired based on the ranges of photon energies of the identified one of the R combinations of N energy images.

4. A system according to claim 2, the processor further to determine distribution functions associated with each of the M different materials by:
- normalization of the N-dimensional coordinates of N values for the voxels of each of the M materials; and
- determination, for each of the M materials, of the first distribution function based on the normalized N-dimensional coordinates.

5. A system according to claim 1, the processor further to determine, based on second N energy images of a volume, a material associated with a voxel of the volume,
- wherein the second N energy images are acquired based on the ranges of photon energies of the identified one of the R combinations of N energy images.

6. A system according to claim 1, further comprising:
- an X-ray detector and an X-ray source operable to acquire the Q energy images of the M different materials.

7. A system according to claim 1, wherein determination of an overlap comprises:
- determination of a Bhattacharyya Coefficient between distribution functions associated with two of the M materials and determined based on the first N energy images.

8. A method comprising:
- acquiring Q (Q≥2) energy images of M (M≥2) different materials, each one of the Q energy images associated with a respective range of photon energies;
- determining R (R≥2) combinations of N (N≥2) energy images from the Q energy images;
- determining an overlap associated with each of the R combinations of N energy images, the overlap associated with a combination of first N energy images indicating an extent of overlap between distribution functions associated with each of the M different materials and determined based on the first N energy images; and
- identifying one of the R combinations of N energy images associated with a smallest overlap of the determined overlaps.

9. A method according to claim 8, wherein determining an overlap associated with a combination of first N energy images comprises:
- determining, for each one of the first N energy images, values corresponding to voxels representing each of the M materials;
- determining an N-dimensional coordinate of N values for the voxels of each of the M materials; and
- determining, for each of the M materials, a distribution function based on the N-dimensional coordinates associated with the M material.

10. A method according to claim 9, further comprising determining, based on the M distribution functions and on second N energy images of a volume, a material associated with a voxel of the volume,
- wherein the second N energy images are acquired based on the ranges of photon energies of the identified one of the R combinations of N energy images.

11. A method according to claim 9, further comprising determining distribution functions associated with each of the M different materials by:
- normalization of the N-dimensional coordinates of N values for the voxels of each of the M materials; and
- determination, for each of the M materials, of the first distribution function based on the normalized N-dimensional coordinates.

12. A method according to claim 8, further comprising determining, based on second N energy images of a volume, a material associated with a voxel of the volume,
- wherein the second N energy images are acquired based on the ranges of photon energies of the identified one of the R combinations of N energy images.

13. A method according to claim 8, further comprising:
- operating an X-ray detector and an X-ray source to acquire the Q energy images of the M different materials.

14. A method according to claim 8, wherein determining an overlap comprises:
- determining a Bhattacharyya Coefficient between distribution functions associated with two of the M materials and determined based on the first N energy images.

15. A system comprising:
- an imaging system to:
  - acquire Q (Q≥2) energy images of M (M≥2) different materials, each one of the Q energy images associated with a respective range of photon energies; and
- a processor to:
  - determine R (R≥2) combinations of N (N≥2) energy images from the Q energy images;
  - determine an overlap associated with each of the R combinations of N energy images, the overlap associated with a combination of first N energy images indicating an extent of overlap between distribution functions associated with each of the M different materials and determined based on the first N energy images; and
  - identify one of the R combinations of N energy images associated with a smallest overlap of the determined overlaps.

16. A system according to claim 15, wherein determination of an overlap associated with a combination of first N energy images comprises:
- determination, for each one of the first N energy images, of values corresponding to voxels representing each of the M materials;
- determination of an N-dimensional coordinate of N values for the voxels of each of the M materials; and
- determination, for each of the M materials, of a distribution function based on the N-dimensional coordinates associated with the M material.

17. A system according to claim 16, the processor further to determine, based on the M distribution functions and on second N energy images of a volume, a material associated with a voxel of the volume,
- wherein the second N energy images are acquired based on the ranges of photon energies of the identified one of the R combinations of N energy images.

18. A system according to claim 16, the processor further to determine distribution functions associated with each of the M different materials by:
- normalization of the N-dimensional coordinates of N values for the voxels of each of the M materials; and
- determination, for each of the M materials, of the first distribution function based on the normalized N-dimensional coordinates.

19. A system according to claim 15, the processor further to determine, based on second N energy images of a volume, a material associated with a voxel of the volume,
- wherein the second N energy images are acquired based on the ranges of photon energies of the identified one of the R combinations of N energy images.

20. A system according to claim 15, wherein determination of an overlap comprises:

determination of a Bhattacharyya Coefficient between distribution functions associated with two of the M materials and determined based on the first N energy images.

* * * * *